United States Patent [19]

Cortina et al.

[11] Patent Number: 4,738,765
[45] Date of Patent: Apr. 19, 1988

[54] ELECTROLYTIC CELL HYGROMETER

[75] Inventors: Vincent B. Cortina, Winchester; Stanley Ronchinsky, Newton Centre; Barbara Offenhartz, Wellesley; Robert T. O'Connor, Holliston, all of Mass.

[73] Assignee: EG&G, Waltham, Mass.

[21] Appl. No.: 872,593

[22] Filed: Jun. 10, 1986

[51] Int. Cl.⁴ .............................................. G01N 27/26
[52] U.S. Cl. ..................... 204/415; 73/335; 73/336.5; 204/430
[58] Field of Search ............. 204/1 W, 415, 418, 430; 73/335, 336, 336.5, 338

[56] References Cited

U.S. PATENT DOCUMENTS

| | | | |
|---|---|---|---|
| 2,047,638 | 7/1936 | Kott | 201/76 |
| 2,937,524 | 5/1960 | Gregor | 73/335 |
| 3,001,918 | 9/1961 | Czuha, Jr. | 204/1 W |
| 3,058,079 | 10/1962 | Jones | 338/35 |
| 3,081,250 | 3/1963 | Hall et al. | 204/430 |
| 3,255,324 | 6/1966 | Ovshinsky | 200/61.04 |
| 3,445,369 | 5/1969 | Porter et al. | 204/415 |
| 3,676,220 | 7/1972 | Ward | 136/86 |
| 3,886,057 | 5/1975 | Bredeweg | 204/1 W |
| 3,891,958 | 6/1975 | Wakabayashi | 338/35 |
| 3,954,590 | 5/1976 | Czuha, Jr. | 204/436 |
| 4,050,995 | 9/1977 | Bredeweg | 204/1 W |
| 4,269,685 | 5/1981 | Parker | 204/415 |
| 4,359,054 | 11/1982 | Leist et al. | 128/635 |
| 4,425,918 | 1/1984 | Moll et al. | 128/635 |
| 4,466,878 | 8/1984 | DiNitto et al. | 204/297 R |

OTHER PUBLICATIONS

Cortina, V., ISA Digitec '85 Show, Apr. 9, 1985, Sales Memo #564.
Cortina, V., Moisture & Humidity Symposium Exhibit Directory, Jan. 25, 1985.
Instrument Society of America, DIGITECH-85, Official Program, May 14-16, 1985.
DewTrace Trace Moisture Analyzer, publicly distributed on or about Apr. 15, 1985.
Keidel, F. A., Determination of Water by Direct Amperometric Measurement, Analytical Chemistry, vol. 31, No. 12, 12/59.
Ronchinsky, S., An Electrochemical Sensor for Trace Moisture in Gases, EG&G, Inc., Waltham, Mass., 1985, pp. 699-706.
Cortina, V., ISA Moisture and Humidity International Conference, Apr. 15-17, 1985, Sales Memo #561.
Cortina, V., Advertising/Sales Promotion Activities-1st Half 1985 Jan. 22, 1985, Sales Memo #562.

Primary Examiner—John F. Niebling
Assistant Examiner—Ben C. Hsing
Attorney, Agent, or Firm—Finnegan, Henderson, Farabow, Garrett, Dunner

[57] ABSTRACT

An electrolytic hygrometer is provided which comprises a hollow cylinder having first and second shoulders and a ceramic substrate containing an electrolytic cell circuit pattern mounted on the second shoulder of the hollow cylinder and extending upwardly inside the hollow cylinder toward the first shoulder. A permeable membrane is provided which is removably mounted on the first shoulder by means of a sandwiched configuration comprising a first mounting ring, a first porous stainless steel protective disk, the membrane, a second porous stainless steel protective disk, and a second mounting ring. A ring nut is employed to removably fasten the membrane's sandwiched configuration against the first shoulder of the hollow cylinder.

3 Claims, 1 Drawing Sheet

U.S. Patent
Apr. 19, 1988
4,738,765
FIG. 1
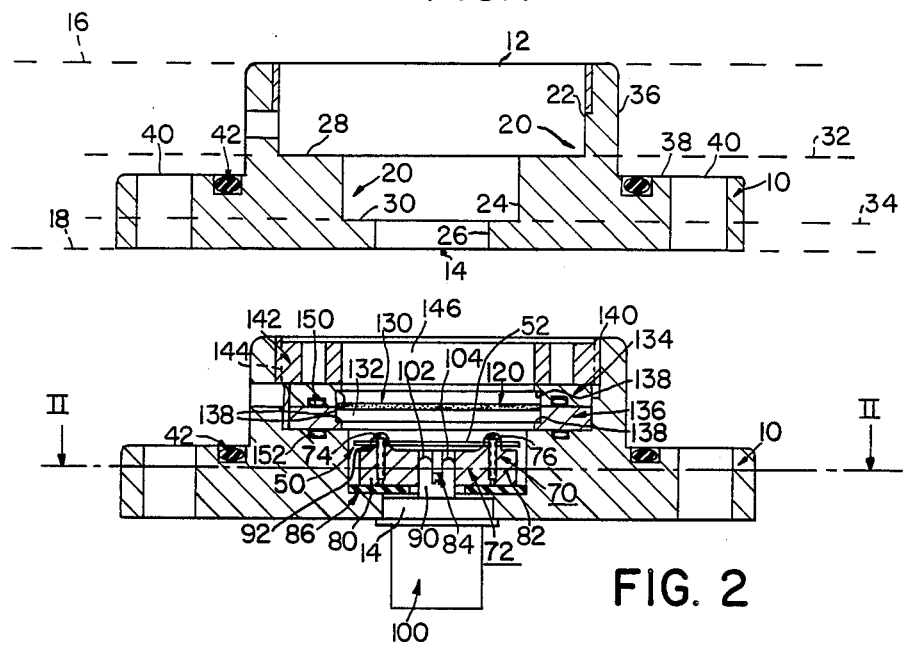
FIG. 2
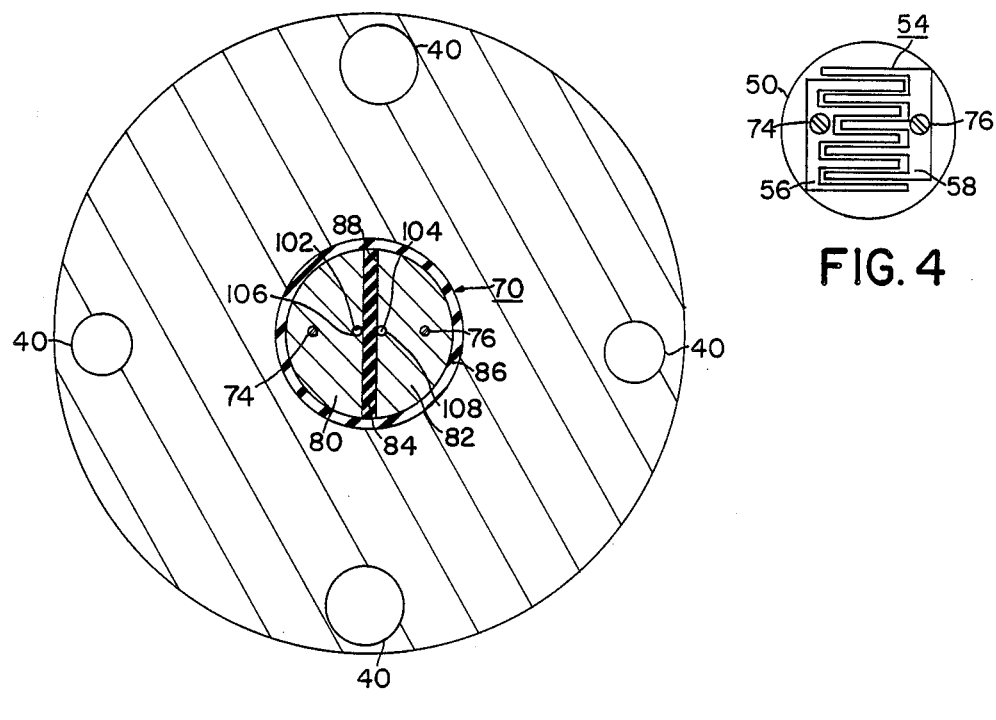
FIG. 4
FIG. 3

ELECTROLYTIC CELL HYGROMETER

BACKGROUND OF THE INVENTION

I. Field of the Invention

The present invention relates to an electrolytic cell hygrometer for measuring moisture levels.

II. Background Information

Electrolytic cell hygrometers are known which employ two electrodes spaced apart one from another to form a circuit pattern on a semiconductor substrate. Each electrode in effect forms one plate of a capacitor on the surface of the substrate. A film of hydroscopic electrolyte, typically, phosphorous pentoxide, is spread over the circuit pattern to fill the space between the electrodes.

Upon application of an electrical potential to the electrodes, the electrolyte, in the absence of water, does not permit current to flow between the electrodes. However, in the presence of water, the electrolyte absorbs moisture and as a consequence becomes conductive thereby permitting current to flow between the electrodes.

As the current flows between the electrodes, moisture absorbed by the electrolyte electrolyzes into hydrogen and oxygen. The electrolyte thus continuously regenerates itself. In addition, the electrical current represents an accurate measurement of the moisture absorbed in accordance with Faraday's Law of Electrolysis.

In addition, a porous membrane may be positioned over the electrodes to form a diffusion barrier between the electrolysis activity occurring in connection with the electrodes and an atmosphere whose moisture content is to be analyzed. This diffusion barrier protects the basic characteristics of the phosphorous pentoxide film and thereby improves operation of the resultant electrolytic cell hygrometer.

However, the porous membrane forming such a diffusion barrier is typically delicate and must be carefully protected. In addition, it is preferable that an electrolytic cell hygrometer employing such membrane have the capacity to not only readily replace the electrode bearing substrate, but also replace the membrane should the membrane become contaminated or if a different form of membrane is desired to be employed. Still further, it is desirable that an electrolytic cell hygrometer be compact and easy to install in an environment where moisture analysis is required.

In view of the foregoing, it is an object of the present invention to provide an electrolytic cell hygrometer of improved physical design which provides for efficient replacement of the diffusion barrier membrane and electrode carrying substrate, while maintaining a compact configuration easily mountable in an atmosphere whose moisture content is to be analyzed.

Additional objects and advantages of the invention will be set forth in the description which follows, and in part will be obvious from that description or may be learned by practice of the invention.

SUMMARY OF THE INVENTION

To achieve the foregoing objects, and in accordance with the purposes of the invention as embodied and broadly described herein, an electrolytic cell hygrometer is provided which comprises a hollow cylinder having open first and second ends lying in parallel first and second planes and having an interior surface which narrows in diameter from the first end to the second end in three step like progressions to form first, second and third interior cylindrical surfaces separated by first and second shoulders having surfaces lying in third and fourth planes, respectively, which are parallel to the first and second planes; a ceramic substrate having an upper surface upon which is mounted an electrolytic cell circuit pattern; means for mounting the substrate on the second shoulder comprising a spacer engaging the second shoulder and extending within the second interior cylindrical surface toward the first shoulder to form a flat surface which lies adjacent the third plane of the first shoulder, and means for removably fastening the substrate on the flat surface of the spacer; an electrical connector extending from the fourth plane within the third interior cylindrical surface and through the second open end of the hollow cylinder, the connector including means for electrically communicating with the circuit pattern of the substrate from outside the hollow cylinder; an electrolytic cell permeable membrane; means for removably mounting the membrane on the first shoulder comprising first and second porous stainless steel disks, one positioned on each side of the membrane to protect and support the membrane, and first and second rings each having a shoulder in the interior cylindrical surface thereof dimensioned to capture the disks therebetween to form a sandwiched configuration of: one ring, one disk, the membrane, the other disk, and the other ring, the rings having an outside cylindrical surface dimensioned to removably slide inside the first interior cylindrical surface of the hollow cylinder to permit the sandwiched configuration to rest on the first shoulder with the membrane positioned adjacent the circuit pattern of the substrate; and means for removably holding the sandwiched configuration in place against the first shoulder comprising first threads formed on the first interior cylindrical surface of the hollow cylinder adjacent the first end of the hollow cylinder and a ring nut having second threads on the outside circumference thereof dimensioned to engage the first threads, the nut further having an opened central portion to permit access to the membrane from outside the hollow cylinder.

Preferably the spacer of the electrolytic cell hygrometer of the subject invention comprises a pair of half circular disks constructed of conductive material, these half circular disks arranged within the second interior cylindrical surface of the hollow cylinder to form a circular disk with a separating channel therebetween; a generally rectangular-shaped electrically insulative spacer positioned in the separating channel between the half circular disks to electrically isolate those disks one from the other; and an electrically insulative washer positioned between the first shoulder and the half circular disks to electrically isolate those disks from the hollow cylinder, the washer having an opening through which the electrical connector may contact the half circular disks.

Furthermore, the means for electrically communicating with the circuit pattern of the subtrate from outside the hollow cylinder preferably comprises at least two conductive pins aligned to extend from the connector through the opening in the washer into electrical contact each with a respective one of the two half circular disks; indents in the half circular disks to receive the pins in electrical contact with the respective one of those disks; and a first electrically conductive fastener passing through the substrate, in electrical contact with a first portion of the pattern on the substrate, and into one of the half circular disks to electrically couple that one disk to the first portion of the pattern and a second electrically conductive fastener passing through the substrate, in electrical contact with a second portion of the pattern on the substrate, and into the other of the half circular disks, to electrically couple that other disk to the second portion of the pattern.

BRIEF DESCRIPTION OF THE DRAWINGS

FIG. 1 is a cross sectional view of the hollow cylinder incorporating the teachings of the present invention;

FIG. 2 is a cross sectional view of an electrolytic cell hygrometer incorporating the teachings of the subject invention;

FIG. 3 is a cross sectional view of the cell hygrometer of FIG. 2 along line II—II; and FIG. 4 is a planar view of the electrical pattern on the substrate of the electrolytic cell hygrometer illustrated in FIG. 2.

DESCRIPTION OF THE PREFERRED EMBODIMENT

Reference will now be made in detail to the present preferred embodiment of the invention as illustrated in the accompanying drawings.

Referring to FIGS. 1 and 2, there is illustrated a hollow cylinder 10 having a first open end 12 and a second open end 14. Open ends 12 and 14 lie in respective parallel first and second planes 16 and 18. Hollow cylinder 10 has an interior surface 20 which narrows in diameter from first end 12 to second end 14 in three step like progressions to form a first interior cylindrical surface 22, a second interior cylindrical surface 24, and a third interior cylindrical surface 26. First interior cylindrical surface 22 is separated from second interior cylindrical surface 24 by first shoulder 28. Second interior cylindrical surface 24 is separated from third interior cylindrical surface 26 by second shoulder 30. Shoulders 28 and 30 have surfaces lying in third and fourth planes 32 and 34, respectively, which are parallel to first and second planes 16 and 18.

Hollow cylinder 10 has an exterior cylindrical surface 36 to which is attached, in the area of second open end 14, an annular flange 38. Flange 38 has a number of holes 40 passing therethrough to facilitate attachment of hollow cylinder 10 to a fixed surface and/or for attachment of a suitable cover to hollow cylinder 10 to close first end 12. In the event such a cover is used, a sealing O-ring 42 is employed adjacent the connection of flange 38 to exterior cylinder 32 to affect a seal between this cover and hollow cylinder 10.

Hollow cylinder 10 may, for example, be constructed of stainless steel. Hollow cylinder 10 may have a height on the order of one inch, the external cylindrical surface 36 of hollow cylinder 10 may have a diameter on the order of two inches, and annular flange 38 have a diameter on the order of three and one quarter inches. Accordingly, hollow cylinder 10 has a compact design facilitating easy installation and use.

As is illustrated in FIGS. 2 and 4, the electrolytic cell hygrometer of the subject invention employs a ceramic substrate 50 having an upper surface 52 upon which is mounted an electrolytic cell circuit pattern 54. As should be well known to those skilled in the art, circuit pattern 54 comprises a first portion 56 which is aligned in interdigitated relation with a second portion 58. Portions 56, 58 have interdigital fingers, preferably having a width and spacing therebetween on the order of four millimeters. In operation, a film of hydroscopic electrolyte, such as phosphorous pentoxide, fills the spaces between first portion 56 and second portion 58 of circuit pattern 54. In the absence of moisture, no current flows between portions 56 and 58. However, when moisture is present, the electrolyte absorbs this moisture and becomes conductive as a consequence thereof, thereby providing electrical conduction between first portion 56 and second portion 58. As current flows between portions 56 and 58, the water in the electrolyte electrolyzes to hydrogen and oxygen. Thus, the electrolyte continuously regenerates itself and, in addition, the electrical current represents an accurate measurement of the moisture absorbed in accordance with Faraday's Law of Electrolysis.

In accordance with the subject invention, means are provided for mounting the ceramic substrate containing an electrolytic cell circuit pattern on a second shoulder of the hollow cylinder. Generically speaking, this means for mounting comprising a spacer engaging the second shoulder of the hollow cylinder and extending within a second interior surface of that cylinder toward the first shoulder to form a flat surface which lies adjacent a third plane defined by the first shoulder, and means for removably fastening the substrate on that flat surface of the spacer.

As illustrated in FIGS. 2 and 3 a mounting mechanism 70 is provided which comprises a spacer 72, and a plurality of conductive screws 74. Spacer 72 further comprises a pair of half circular disks 80, 82, insulative spacer 84, and insulative washer 86. The half circular disks 80, 82 are constructed of conductive material, preferably stainless steel. Half circular disks 80, 82 are arranged within second interior surface 24 of hollow cylinder 10 to form a circular disk having a separation channel 88. Insulative spacer 84 is preferably constructed of teflon and is generally rectangular in cross sectional area. Spacer 84 is dimensioned to fit within separation channel 88 between half circular disks 80, 82 to electrically isolate disks 80, 82 one from the other. Insulative washer 86 is positioned between first shoulder 30 of hollow cylinder 10 and half circular disks 80, 82 to electrically isolate disks 80, 82 from hollow cylinder 10. Washer 86 has a central opening 90 through which access may be had to disks 80 and 82 from outside hollow cylinder 10 through second opening 14.

Thus, spacer 72, comprising half circular disks 80, 82, insulative spacer 84 and insulative washer 86, engages second shoulder 30 and extends within second interior cylindrical surface 24 toward first shoulder 28 of hollow cylinder 10. In addition, the upper portions of circular disks 80, 82 and insulative spacer 84 form a flat surface which lies adjacent third plane 32 of first shoulder 28. Ceramic substrate 50 is mounted on this upper surface adjacent, yet slightly below, plane 32 through utilization of conductive screws 74, 76. A washer or spring 92 may be employed between substrate 50 and the upper surface of spacer 72. Preferably washer or spring 92 is also conductive.

As may be seen in FIG. 4, conductive screw 74 is in contact with first portion 56 of circuit pattern 54 and conductive screw 76 is in contact with second portion 58 of circuit pattern 54. Thus, screw 74 provides an electrically conductive path from first portion 56 to half circular disk 80 and screw 76 provides an electrically conductive path from second portion 58 to half circular disk 82. As a consequence, screws 74, 76 have the dual function of providing a mechanism for removably fastening substrate 50 to spacer 72 and of providing electrical contact from selective portions of circuit pattern 52 to each of respective disks 74, 76.

As is further illustrated in FIG. 2 an electrical connector 100 extends from fourth plane 34 within third interior cylindrical surface 26 and through second open end 14 of hollow cylinder 10. Connector 100 includes a mechanism for electrically communicating with circuit pattern 54 of substrate 50 from outside hollow cylinder 10. This mechanism comprises conductive pins 102 and 104; corresponding indents and/or holes 106 and 108 in disks 80, 82; and conductive screws 74 and 76.

Specifically, at least two conductive pins 102, 104 are aligned to extend from the upper surface of connector 100 through central opening 90 of insulative washer 86 and into electrical contact each with a respective one of half circular disks 80, 82. This electrical contact is achieved by engagement of pins 102, 104 with respective indents or holes 106, 108 of half circular disks 80, 82. Thus, full electrical contact is made from electrical connector 100, through pins 102, 104, through half circular disks 80, 82, through conductive screws 74, 76, to respective portions 56, 58 of circuit pattern 54.

As is illustrated in FIG. 2, the electrolytic cell hygrometer of the subject invention employs an electrolytic cell permeable membrane 120. As is known to those skilled in the art, membrane 120 forms a diffusion barrier such that the mass transport rate of moisture across this diffusion barrier is proportionate to the water content measured through operation of circuit pattern 54. Membrane 120 preferably comprises a silicon polycarbonate copolymer laminate of 1 millimeter thickness to form a hydrophobic membrane which allows for diffusion of water vapor due to partial differential pressure in one direction across the membrane and allows for diffusion of by-products in the opposite direction across the membrane.

To protect the membrane of the subject invention, and in order to enable efficient and economic replacement of that membrane, in accordance with the subject invention there is provided means for removably mounting that membrane on the first shoulder of the hollow cylinder housing of the subject invention.

As is illustratively shown in FIG. 2 a mounting mechanism is provided which comprises first and second porous stainless steel disks 130, 132 and first and second mounting rings 134, 136. Porous disks 130, 132 are preferably constructed of sintered stainless steel and have a diameter corresponding to the diameter of permeable membrane 120. Porous disks 130, 132 are positioned one on each side of membrane 120 to protect and support membrane 120.

Mounting rings 134, 136 each have a shoulder 138 on the interior cylindrical surface thereof dimensioned to capture porous disks 130, 132 therebetween to form a sandwich configuration of ring 134, porous disk 130, membrane 120, porous disk 132, and ring 136. Rings 134 and 136 have an outside cylindrical surface dimensioned to removably slide inside first interior cylindrical surface 22 of hollow cylinder 10 to permit the resultant sandwich configuration to rest on first shoulder 28 of hollow cylinder 10, with membrane 120 being thereby positioned adjacent circuit pattern 54 of ceramic substrate 50.

Further in accordance with the subject invention there is provided means for removably holding the above-mentioned sandwich configuration in place against the first shoulder of the hollow cylinder of the subject invention.

Specifically, as is illustrated in FIG. 2 there is provided first threads 140, a ring nut 142, and second threads 144. First threads 140 are formed on the first interior cylindrical surface 22 of hollow cylinder 10 adjacent first end 12 of hollow cylinder 10. Second threads 144 are formed on the outside circumference of ring nut 42 and are dimensioned to removably engage first threads 140. Ring nut 142 has an opened central portion 146 to permit access to membrane 120 from outside hollow cylinder 10. Thus, ring 142 may be tightened down onto the sandwiched configuration comprising porous disk 130, mounting ring 134, membrane 120, porous disk 132, and mounting ring 136 to removably hold that sandwiched configuration in position against first shoulder 28 of hollow cylinder 10. To provide effective sealing, an O-ring 150 may be located between rings 134 and 136, and an O-ring 152 may be positioned between mounting ring 136 and first shoulder 28.

Accordingly, there is provided an electrolytic cell hygrometer in which a moisture analyzing cell pattern is protected by a diffusion membrane and in which both the cell pattern and the diffusion membrane are easily accessible and replaceable.

Additional advantages and modifications will readily occur to those skilled in the art. The invention in its broader aspects is, therefore, not limited to the specific details, representative apparatus, and illustrative examples shown and described. Accordingly, departures may be made from such details without departing from the spirit or scope of applicant's general inventive concept as claimed.

I claim:

1. An electrolytic cell hygrometer comprising:
   a. a hollow cylinder having open first and second ends lying in parallel first and second planes and having an interior surface which narrows in diameter from said first end to said second end in three step-like progressions to form first, second and third interior cylindrical surfaces separated by first and second shoulders having surface lying in third and fourth planes, respectively, which are parallel to said first and second planes;
   b. a ceramic substrate having an upper surface upon which is mounted an electrolytic cell circuit pattern;
   c. means for mounting said substrate on said second shoulder comprising a spacer engaging said second shoulder and extending within said second interior cylindrical surface toward said first shoulder to form a flat surface which lies adjacent said third plane of said first shoulder, and means for removably fastening said substrate onto said flat surface of said spacer;
   d. an electrical connector extending from said fourth plane within said third interior cylindrical surface and through said second open end of said hollow cylinder, said connector including means for electrically communicating with said circuit pattern of said substrate from outside said hollow cylinder;
   e. an electrolytic cell permeable membrane;
   f. means for removably mounting said membrane on said first shoulder comprising first and second porous stainless steel disks, one positioned on each side of said membrane to protect and support said membrane; and first and second rings each having a shoulder in the interior cylindrical surface thereof dimensioned to capture said disks therebetween to form a sandwiched configuration of one ring, one disk, said membrane, the other disk, and the other ring, said rings having an outside cylindrical surface dimension to removably slide inside said first interior cylindrical surface of said hollow cylinder to permit said sandwiched configuration to rest on said first shoulder with said membrane positioned adjacent said circuit pattern of said substrate; and g. means for removably holding said sandwiched configuration in place against said first shoulder comprising first threads formed on said first interior cylindrical surface of said hollow cylinder adjacent said first end of said hollow cylinder and a ring nut having second threads on the outside circumference thereof dimensioned to engage said first threads, said nut further having an open central portion to permit access to said membrane from outside said hollow cylinder.

2. An electrolytic cell hygrometer of claim 1 wherein said spacer comprises:
   i. a pair of half circular disks constructed of conductive material, said half circular disks being arranged within said second interior cylindrical surface of said hollow cylinder to form a circular disk having a separation channel;
   ii. a generally rectangular shaped electrically insulative spacer positioned in said separation channel between said half circular disks to electrically isolate said disks one from the other; and
   iii. an electrically insulative washer positioned between said first shoulder and said half circular disks to electrically insulate said disks from said hollow cylinder, said washer having an opening through which said electrical connector contacts said half circular disks.

3. An electrolytic cell hygrometer of claim 2 wherein said means for electrically communicating with said circuit pattern of said substrate from outside said hollow cylinder comprises:
   i. at least two conductive pins aligned to extend from said connector through said opening in said washer into electrical contact each with a respective one of said two half circular disks;
   ii. indents in said half circular disks to receive said pins in electrical contact with said respective disks; and
   iii. a first electrically conductive fastener passing through said substrate, in electrical contact with said first portion of said pattern on said substrate, and into one of said half circular disks to electrically couple said one of said half circular disks to said first portion of said pattern, and a second electrically conductive fastener passing through said substrate, in electrical contact with a second portion of said pattern of said substrate, and into the other of said half circular disks, to electrically couple said other of said half circular disks to said second portion of said pattern.

* * * * *